(12) United States Patent
Mehlberg

(10) Patent No.: US 9,073,806 B2
(45) Date of Patent: Jul. 7, 2015

(54) FLUID CATALYTIC CRACKING SYSTEM AND PROCESS

(71) Applicant: UOP LLC, Des Plaines, IL (US)

(72) Inventor: Robert L. Mehlberg, Wheaton, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/602,960

(22) Filed: Jan. 22, 2015

(65) Prior Publication Data

US 2015/0133710 A1    May 14, 2015

Related U.S. Application Data

(62) Division of application No. 12/340,291, filed on Dec. 19, 2008, now Pat. No. 8,940,955.

(51) Int. Cl.
*C10G 11/00* (2006.01)
*C07C 4/06* (2006.01)

(52) U.S. Cl.
CPC ............... *C07C 4/06* (2013.01); *C07C 2529/40* (2013.01)

(58) Field of Classification Search
None
See application file for complete search history.

(56) References Cited

U.S. PATENT DOCUMENTS 5,538,625 A * 7/1996 Sigaud et al. ............... 208/127
6,682,705 B1 * 1/2004 Gross et al. ................. 422/139

* cited by examiner

*Primary Examiner* — In Suk Bullock
*Assistant Examiner* — Sharon Pregler
(74) *Attorney, Agent, or Firm* — James C. Paschall

(57) ABSTRACT

One exemplary embodiment can be a fluid catalytic cracking system. The system can include a reaction zone, in turn including a reactor receiving, a fluidizing stream, a fuel gas stream, a fluidizable catalyst, a stream having an effective amount of oxygen for combusting the fuel gas stream, and a feed.

2 Claims, 1 Drawing Sheet

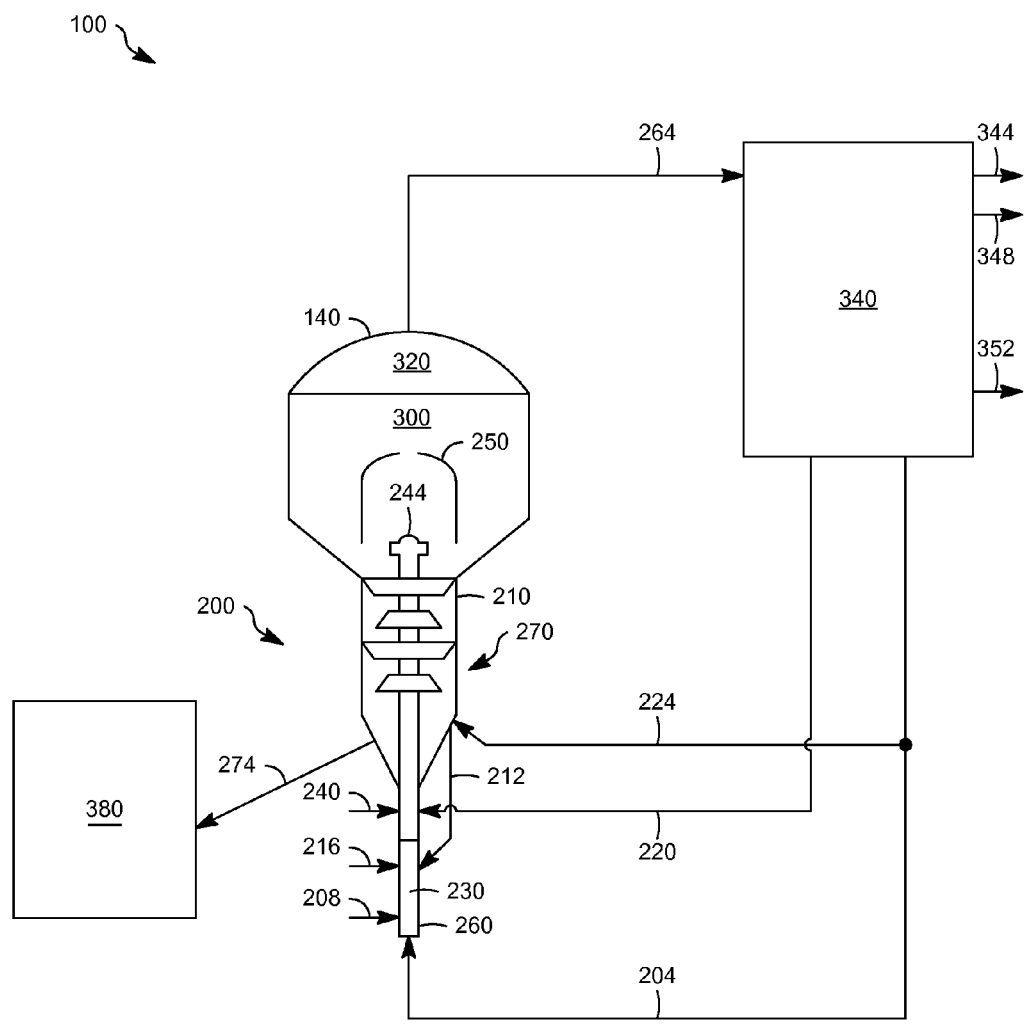

FLUID CATALYTIC CRACKING SYSTEM AND PROCESS

CROSS-REFERENCE TO RELATED APPLICATION

This application is a Division of copending application Ser. No. 12/340,291 filed Dec. 19, 2008, the contents of which are hereby incorporated by reference in its entirety.

FIELD OF THE INVENTION

This invention generally relates to a fluid catalytic cracking system and process.

DESCRIPTION OF THE RELATED ART

Cracking processes, such as fluid catalytic cracking (hereinafter may be abbreviated "FCC"), can produce different products, such as gasoline and light olefins, e.g., propylene. In some instances, it is desired to produce propylene along with the gasoline product in a single reactor. Unfortunately, often producing both products simultaneously can limit the production of one product or the other. In addition, there may be some undesired side reactions.

One solution is to provide a separate reactor for producing light olefins, such as propylene and ethylene. In such reactors, the feed and process conditions can be tailored to maximize the light olefin yield. Unfortunately, such dedicated reactors require additional capital in addition to a reactor vessel, such as a furnace, heat exchangers, and other equipment. As a consequence, it would be desirable to minimize the added capital expense of producing more than one FCC product.

SUMMARY OF THE INVENTION

One exemplary embodiment can be a fluid catalytic cracking system. The system can include a reaction zone, in turn including a reactor receiving a fluidizing stream, a fuel gas stream, a fluidizable catalyst, a stream having an effective amount of oxygen for combusting the fuel gas stream, and a feed.

Another exemplary embodiment may be a fluid catalytic cracking system. The system can include a reaction zone, in turn including a riser receiving a stream. The stream may have an effective amount of oxygen for combusting a fuel gas.

Yet another exemplary embodiment can be a process for combusting a fuel gas in a reaction zone of a fluid catalytic cracking system. The process may include introducing a hydrocarbon feed, the fuel gas, and a stream having an effective amount of oxygen for combusting the fuel gas.

The embodiments disclosed herein can provide a reactor with conditions dedicated to selectively convert heavier hydrocarbons into lighter compounds, such as propylene and ethylene. As such, the reactor can be provided with a higher level of the desired catalyst for converting such feeds. In addition, the embodiments disclosed herein can provide a system that eliminates additional equipment, such as a furnace. Such a reduction in capital costs can improve the efficiency of modifying or adding such an additional reactor to an existing unit, or reducing the expense of a new design.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1, C_2, C_3 \ldots C_n$ where "n" represents the number of carbon atoms in the one or more hydrocarbon molecules. Furthermore, a superscript "+" or "−" may be used with an abbreviated one or more hydrocarbons notation, e.g., $C_3^+$ or $C_3^-$, which is inclusive of the abbreviated one or more hydrocarbons. As an example, the abbreviation "$C_3^+$" means one or more hydrocarbon molecules of three carbon atoms and/or more.

As used herein, the term "rich" can mean an amount of generally at least about 50%, and preferably about 70%, by mole, of a compound or class of compounds in a stream.

As used herein, the term "butene," can collectively refer to 1-butene, cis-2-butene, trans-2-butene, and/or isobutene.

As used herein, the term "downstream" generally means a location spaced apart from another location in the direction of a flow of a stream. As an example, a first point that is at a higher elevation on a riser than a second point would be downstream from the second point if an upward flowing feed is provided at the bottom of the riser.

BRIEF DESCRIPTION OF THE DRAWING

FIG. 1 is a schematic depiction of an exemplary fluid catalytic cracking system.

DETAILED DESCRIPTION

Referring to FIG. 1, an exemplary fluid catalytic cracking system 100 can include a reaction zone or a first reaction zone 200, a stripping zone 270, a disengagement zone 300, a separation zone 340, and a regeneration zone or another reaction zone 380. Moreover, process flow lines in the FIGURES can be referred to as lines, pipes, conduits, feeds, fluidized catalyst, or streams. Particularly, a line, a pipe, or a conduit can contain one or more feeds, fluidized catalyst, or streams, and one or more feeds, fluidized catalyst, or streams can be contained by a line, a pipe, or a conduit.

Particularly, the reaction zone 200 can include a riser reactor 210, which in turn, can have a reactor or reaction vessel 250 receiving a riser 260. Alternatively, the reaction zone 200 can include a fluidized bed. Generally, the reaction zone 200, particularly the riser 260, can operate at any suitable conditions, such as a temperature of about 425° to about 705° C., or preferably greater than about 650° C. In addition, the riser 260 can operate at a pressure of about 40 to about 700 kPa. Furthermore, the reaction zone 200 may be operated at a low hydrocarbon partial pressure. Particularly, the hydrocarbon partial pressure can be about 30 to about 180 kPa, preferably about 60 to about 140 kPa. Alternatively, the hydrocarbon partial pressure can be less than about 180 kPa, such as less than about 110 kPa, or preferably less than about 70 kPa. In one exemplary embodiment, the hydrocarbon partial pressure can be about 5 to about 110 kPa.

The riser 260 can receive a variety of streams, namely a fluidizing stream 204, a fuel gas stream or fuel gas 208, a fluidizable catalyst 212, a stream including an effective amount of oxygen 216, a recycled olefin stream 220, and a hydrocarbon feed 240.

The riser 260 can further define a combustion zone 230. Typically, the combustion zone 230 receives the fluidizing stream 204, fuel gas stream 208, fluidizable catalyst 212, and oxygen stream 216. The materials in the equipment surrounding the combustion zone 230 can have specialized metallurgy, refractory, and cleanliness specifications to handle an oxygen stream 216 having greater than, e.g., about 30% oxygen, by mole.

The fuel gas or fuel gas stream 208 can contain any suitable material for combustion. Particularly, the fuel gas stream 208 can include at least one of hydrogen, nitrogen, carbon monoxide, methane, ethane, ethylene, propane, propylene, butane, and butene. The oxygen stream 216 can include an amount of oxygen effective for combusting the fuel gas stream 208. Particularly, the stream 216 can contain at least about 5%, at least about 20%, at least about 29% and at least about 99%, by mole, oxygen. In one exemplary embodiment, the oxygen stream 216 can include air.

Generally, the combustion zone 230 heats the catalyst to a suitable temperature, such as at least above about 650° C. The fuel gas stream 208 can be obtained from any suitable source, such as off-gas from the separation zone 340, as hereinafter described, and/or carbon monoxide and carbon dioxide by-products of hydrogen purification. Different fuel gas streams 208 can be utilized depending on the desired effects. Particularly, heating the process by direct contact with a fuel gas combined with steam or carbon dioxide can minimize coking by olefins in high temperature heat exchangers. Also, using a fuel gas with very limited added oxygen can potentially minimize steam partial pressure, temperature rise, and associated hydrothermal deactivation of the catalyst, especially when operating the process at high catalyst circulation rates to minimize catalyst temperature rise. In addition, using the fuel gas stream 208 with low hydrocarbon, such as olefin, partial pressures at a high total process pressure may minimize the gas compression ratio. Alternatively, an oxygen stream 216 can have a high oxygen concentration minimizing purge losses from the process and nitrogen dilution of the reaction products.

The fluidizable catalyst 212 can include regenerated catalyst, spent catalyst, make-up catalyst or a combination thereof. Although the catalyst 212 is depicted as being recycled from the disengagement zone 300 through, e.g., a standpipe and slide valve, make-up and/or regenerated catalyst can be added or provided to the pipe 212 and/or at the riser 260. The fluidizable catalyst 212 can be subject to reheating and a mixture of a first catalyst having pores with openings greater than about 0.7 nm and a catalyst having smaller openings than the first catalyst. Such catalyst mixtures are disclosed in, e.g., U.S. Pat. No. 7,312,370 B2. It is generally preferable that the catalyst mixture include a high amount, if not all, of the smaller pore catalyst, such as ZSM-5, to enhance light olefin yields. In addition, a catalyst, such as ZSM-5, does not coke to a significant extent thereby removing the requirement of a regeneration zone. As such, burning in the combustion zone 230 can suffice to remove any coke build-up.

Generally, the first catalyst may include any of the well-known catalysts that are used in the art of FCC, such as an active amorphous clay-type catalyst and/or a high activity, crystalline molecular sieve. Zeolites may be used as molecular sieves in FCC processes. Preferably, the first catalyst includes a large pore zeolite, such as a Y-type zeolite, an active alumina material, a binder material, including either silica or alumina, and an inert filler such as kaolin.

Typically, the zeolitic molecular sieves appropriate for the first catalyst have a large average pore size. Usually, molecular sieves with a large pore size have pores with openings of greater than about 0.7 nm in effective diameter defined by greater than 10, and typically 12, member rings. Pore Size Indices of large pores can be above about 31. Suitable large pore zeolite components may include synthetic zeolites such as X and Y zeolites, mordent and faujasite. Y zeolites with a rare earth content of no more than about 1.0 weight percent (hereinafter may be abbreviated "wt %") rare earth oxide on the zeolite portion of the catalyst may be preferred as the first catalyst.

The second catalyst may include a medium or smaller pore zeolite catalyst exemplified by ZSM-5, ZSM-11, ZSM-12, ZSM-23, ZSM-35, ZSM-38, ZSM-48, and other similar materials. Other suitable medium or smaller pore zeolites include ferrierite, and erionite. The second catalyst preferably has the medium or smaller pore zeolite dispersed on a matrix including a binder material such as silica or alumina and an inert filler material such as kaolin. The second catalyst may also include some other active material such as Beta zeolite. These compositions may have a crystalline zeolite content of about 10 to about 50 wt % or more, and a matrix material content of about 50 to about 90 wt %. Preferably, compositions can contain about 40 wt % crystalline zeolite material, and those with greater crystalline zeolite content may be used, desirably if they have satisfactory attrition resistance. Generally, medium and smaller pore zeolites are characterized by having an effective pore opening diameter of less than or equal to about 0.7 nm, rings of 10 or fewer members, and a Pore Size Index of less than 31.

The total mixture may contain about 1 to about 25 wt % of the second catalyst, namely a medium to small pore crystalline zeolite with greater than or equal to about 1.75 wt % being preferred. When the second catalyst contains about 40 wt % crystalline zeolite with the balance being a binder material, the mixture may contain about 4 to about 40 wt % of the second catalyst with a preferred content of at least about 7 wt %. The first catalyst may comprise the balance of the catalyst composition. Usually, the relative proportions of the first and second catalysts in the mixture will not substantially vary throughout the FCC system 100. The high concentration of the medium or smaller pore zeolite as the second catalyst of the catalyst mixture can improve selectivity to light olefins.

The fluidizing stream 204 can also have the same composition or substantially a similar composition as a stripping gas stream 224, as hereinafter described. The fluidizing stream 204 can have any suitable composition, and typically can include light hydrocarbons such as $C_1$-$C_4$, as well as steam, nitrogen, hydrogen sulfide, fuel gas, carbon monoxide, and carbon dioxide. Alternatively, the stream 204 can be treated to have the hydrogen sulfide and/or other gases removed. Generally, the fluidizing stream 204 is sufficient to lift the fluidizable catalyst through the combustion zone 230 upwards through the riser 260 to the reaction vessel 250.

The gas and catalyst exiting the combustion zone 230 desirably have a low oxygen content. Particularly, the combustion zone 230 generally has a sufficient residence time for combusting substantially all the oxygen. So, the oxygen content can be less than about 1%, preferably less than about 0.1%, by mole.

After exiting the combustion zone 230, a feed 240 can be provided to the riser. Generally, the feed 240 is preheated to a temperature of at least about 300° C., preferably about 400° to about 550° C., and optimally about 400° to about 490° C. Generally, it is desirable that the hydrocarbon feed 240 be a gas. The hydrocarbon feed 240 can include at least about 50%, by mole, of the components as a gas. Preferably, the entire hydrocarbon feed 240, e.g., at least about 99%, by mole, is a gas.

Generally, the feed 240 can have an effective amount of one or more $C_4$-$C_7$ hydrocarbons for producing propylene. Preferably, at least about 10 wt % of the feed 240 is olefinic. In other preferred embodiments, at least about 60 to about 70 wt % of the feed 240 may be olefinic. In addition, optionally a recycle stream 220 can be provided to the riser 260. The olefin stream 220 can, independently, have generally the same composition as the feed 240. In one preferred embodiment, the recycled olefin stream 220 can have $C_4$ olefins, preferably $C_4$ and/or $C_6$ olefins for increasing the yield of a desired light olefin, such as propylene. Afterwards, the mixture of catalyst and feed can rise upwards to the one or more swirl arms 244 at the termination of the riser 260. The one or more swirl arms 244 can separate one or more hydrocarbon products, such as a propylene product, from the catalyst. Generally, although the swirl arms 244 can separate the catalyst from the hydrocarbon within the reaction vessel 250, reactions may still be ongoing due to contact between at least some of the catalyst and at least some of the hydrocarbon.

Afterwards, the hydrocarbon and some of the remaining entrained catalyst can enter the disengagement zone 300. Generally, the disengagement zone 300 can include any suitable disengagement device, such as a cyclone separator unit. The cyclone separator unit can include any suitable number of cyclones for removing the remaining catalyst particles from the product hydrocarbon stream. Thus, the catalyst can be separated and through dip legs dropped to the lower regions of a shell 140. Subsequently, the catalyst can enter a stripping zone 270 via openings in the reaction vessel 250 where the addition of a stripping gas can strip interstitial hydrocarbons and absorbed hydrocarbons from the surface of the catalyst by counter-current contact. Generally, the stripping gas stream 224 is a pre-heated fuel gas or recycled gas from the separation zone 340 to minimize hydrothermal deactivation. Alternatively, the stripping gas can be steam. Such cyclone separators and stripping zones are disclosed in, for example, U.S. Pat. No. 7,312,370 B2.

Afterwards, the catalyst can continue to flow downward outside the at least one riser 260 within the reaction vessel 250 until it reaches a first catalyst conduit 274, which can transfer catalyst from the at least one reaction vessel 250 to a regeneration zone or another reaction zone 380. If the zone 380 is for regenerating, the zone 380 can operate at any suitable temperature, such as above 650° C. or other suitable conditions for removing coke accumulated on the catalyst particles. Subsequently, the regenerated catalyst can be returned to another FCC system, or at least a portion of the catalyst can be returned to the riser 260 by, e.g., communicating the regenerated catalyst with the fluidizing catalyst line 212. Any suitable regeneration zone can be utilized, such as those disclosed in, for example, U.S. Pat. Nos. 4,090,948 and 4,961,907.

Alternatively, the zone 380 can be another reaction zone, such as an FCC unit that is processing heavier hydrocarbons, such as a vacuum gas oil and/or an atmospheric residue. In such an instance, the spent catalyst can be utilized for further cracking operations, and may subsequently be regenerated from that reaction zone 380.

The disengagement zone 300 can also provide the one or more hydrocarbon products, such as ethylene and/or propylene, which may pass to a plenum 320 of the shell 140. Subsequently, the one or more hydrocarbon products can exit via a line 264 to the separation zone 340. Optionally, the one or more products in the line 264 can be cooled by quenching with or by indirect heat exchange with other streams to preheat them, e.g., the feed 240 and/or the recycle stream 220, or other process streams.

Generally, the separation zone 340 can receive the products from the disengagement zone 300. Typically, the separation zone 340 can include one or more distillation columns. Such systems are disclosed in, for example, U.S. Pat. No. 3,470,084. Usually, the separation zone 340 can produce one or more products, such as an off-gas 344, which can optionally be recycled to the riser 260 and can at least partially comprise the fuel gas stream 208. Other products can include a stream 348 including light olefins, such as ethylene and propylene, and heavier hydrocarbons, such as $C_4^+$ hydrocarbons and catalyst fines, in a stream 352. The stream 352 can optionally be recycled to another FCC unit that handles heavier feeds, such as a vacuum gas oil or an atmospheric residue. If the zone 380 is another reaction zone 380, the stream 352 can be at least partially routed to that zone 380.

Thus, the system 100 can prevent carbon build-up on the catalyst and provide process heat without furnaces and associated emissions at conditions that can minimize hydrothermal deactivation of the catalyst and dilution of the light olefin product. As such, the system 100 can operate independently of a fluid catalytic cracking unit processing heavier feeds, while taking advantage of the fluid catalytic cracking unit waste heat, if available. Particularly, such heat can be used to preheat the feed 240 to the riser 260. In the combustion zone 230, not only can the catalyst be heated, but it also may be regenerated to remove small amounts of coke on the catalyst.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for combusting a fuel gas in a reaction zone of a fluid catalytic cracking system, comprising introducing a hydrocarbon feed, the fuel gas, and a stream comprising an effective amount of oxygen for combusting the fuel gas
   wherein the riser receives the fuel gas, the oxygen stream downstream of the fuel gas, and the hydrocarbon feed downstream of the oxygen stream.

2. The process according to claim 1, wherein the oxygen stream comprises air.

* * * * *